United States Patent [19]
Vanier et al.

[11] Patent Number: 5,828,405
[45] Date of Patent: Oct. 27, 1998

[54] GEMSTONE REGISTRATION SYSTEM

[75] Inventors: Dana J. Vanier, Ottawa; Hermann F. Wallner, Richmond; Michael Leydon, Saskatoon, all of Canada

[73] Assignee: Omphalos Recovery Systems Inc., Saskatoon, Canada

[21] Appl. No.: 745,361

[22] Filed: Nov. 8, 1996

[30] Foreign Application Priority Data

Nov. 9, 1995 [CA] Canada ................................ 2162532

[51] Int. Cl.$^6$ ..................................... H04N 7/18
[52] U.S. Cl. ............................. 348/61; 348/161; 356/30
[58] Field of Search ............................ 348/61, 79, 125, 348/131, 161; 356/30; 382/109; H04N 7/18

[56] References Cited

U.S. PATENT DOCUMENTS

| | | | |
|---|---|---|---|
| 3,947,120 | 3/1976 | Bar-Issac | 356/30 |
| 4,728,770 | 3/1988 | Kaprelian | 219/21 |
| 5,015,090 | 5/1991 | Weisman et al. | 356/30 |
| 5,124,935 | 6/1992 | Wallner | 356/30 |
| 5,379,102 | 1/1995 | Takeuchi | 356/30 |
| 5,422,711 | 6/1995 | Can | 356/30 |
| 5,430,538 | 7/1995 | Kobayashi | 356/30 |
| 5,544,254 | 8/1996 | Hartley | 356/30 |
| 5,615,005 | 3/1997 | Valente | 356/30 |

FOREIGN PATENT DOCUMENTS

| | | |
|---|---|---|
| 2081439 | 2/1982 | United Kingdom . |
| 9209882 | 6/1992 | WIPO . |
| 9312496 | 6/1993 | WIPO . |
| 9511447 | 4/1995 | WIPO . |
| 9623207 | 8/1996 | WIPO . |

*Primary Examiner*—Howard W. Britton

[57] ABSTRACT

The gemstone recordal and retrieval system records optical images for gemstones in an effective manner. The optical image of a gemstone is captured using a two-dimensional charge coupled device whereby the time to capture the image is relatively short. The optical images can be improved in definition by varying the output of a laser LED. This fast feedback and adjustability provides accurate recordings.

13 Claims, 4 Drawing Sheets

ISi Compare Verification Confidence Return.

Green dots: reflect the original gemprint.
Red dots: reflect the comparison gemprint.
Blackdots: overlapping (matching) dots of both images.
Note: The Print button is now enabled.

GEMSTONE REGISTRATION SYSTEM

FIELD OF THE INVENTION

The present invention relates to a system for classifying and recording information with respect to gemstones and providing an owner with an accurate optical identification of the gemstone. The invention also relates to a verification system for jewellers.

BACKGROUND OF THE INVENTION

Gemstones have their own unique optical response and this optical response can be used for accurate identification of the gemstones. In this regard, U.S. Pat. No. 3,947,120 discloses an arrangement for providing an optical fingerprint of a gemstone where a laser beam is focused on a gemstone and the optical response of the gemstone is recorded on a recording medium, preferably a photographic medium. This arrangement provides a fingerprint of the gemstone which is reproducible and has been held by the courts to be sufficient evidence to prove that the gemstone under consideration having a certain optical response is the same as a previously identified gemstone having essentially the same optical response.

This prior art structure used a photographic medium and the actual record was sensitive to the exposure period as well as the power of the laser.

European Application No. 0 042 361 discloses a device for producing a reproducible identification pattern of a polished gemstone in which collimated light is directed onto the gemstone and the directions of the refracted and reflected light beams are determined.

Our own PCT application No. PCT/CA91/00424 discloses improvements to systems for recording the optical fingerprint of gemstones.

The prior art arrangements require considerable time to collect the information associated with the optical response from the gemstone and these arrangements have not allowed a user a great deal of adjustment to improve the optical response.

The present invention discloses a new system and apparatus for overcoming a number of deficiencies with respect to the prior art.

SUMMARY OF THE INVENTION

A gemstone recordal system according to the present invention records a unique light pattern of a gemstone. The system comprises a site computer having means for receiving and displaying a data signal from a two-dimensional video camera. The two-dimensional video camera is part of a light image capture arrangement additionally comprising a laser diode in combination with optical means for producing a collimated light beam directed at a gemstone fixture. The gemstone fixture orientates a gemstone in a predetermined manner relative to the collimated light beam, and a screen surface is located to collect and display the unique light pattern from a gemstone. The video camera directed at the screen surface and is sized to capture the unique pattern simultaneously. The computer corrects the signal from the video camera for known distortions introduced due to an angular position of the video camera relative to the screen surface and producing a digital signal of the unique pattern on said computer for review and approval by a user. The computer includes means to input and associate characteristics of the gemstone producing the image with the digital signal thereby producing a combined signal. A printer is provided for producing a certificate identifying the characteristics and reproducing the corrected unique pattern. The computer forms a communication link with a predetermined computer database and outputs the combined signal to the predetermined computer database which records the combined signal in a standardized manner.

According to an aspect of the invention, the predetermined computer database, upon recordal of a combined signal, transmits an acknowledgement signal back to the site computer.

According to a further aspect of the invention, the signal from the video camera is displayed on a display screen of said site computer.

According to an aspect of the invention, the diode laser has an adjustable control for varying the output thereof to accommodate different light absorbing properties of gemstones and different ambient conditions.

According to a further aspect of the invention, the site computer evaluates each captured image and has an actuation control which adjusts said adjustable control means of the laser.

According to a further aspect of the invention, the system includes means for entering an appraised value of the gemstone at the site computer and the predetermined computer database reviews the appraised value based on said characteristics and with reference to industry averages and accepts said appraised value when the appraised value is consistent with industry averages for a similar gemstone and otherwise flags the appraised value.

A device for producing a reproducible identification pattern of a polished gemstone according to the present invention comprises light directing means for directing a collimated beam of light onto a gemstone orientated in a particular known manner to produce an optical output of the internal refraction and reflection characteristics of the gemstone, means for capturing a selected portion of the output in a manner to establish the relative size and location of the reflected light beams, characterized in that the capturing means is a video camera.

According to an aspect of the invention, the light directing means of the device is a laser diode having associated therewith optical means for collimating the output.

According to a further aspect of the invention, the laser diode has an adjustable power control for varying the light output thereof.

BRIEF DESCRIPTION OF THE DRAWINGS

Preferred embodiments of the invention are shown in the drawings, wherein.

DETAILED DESCRIPTION OF THE PREFERRED EMBODIMENTS

Figure 1:
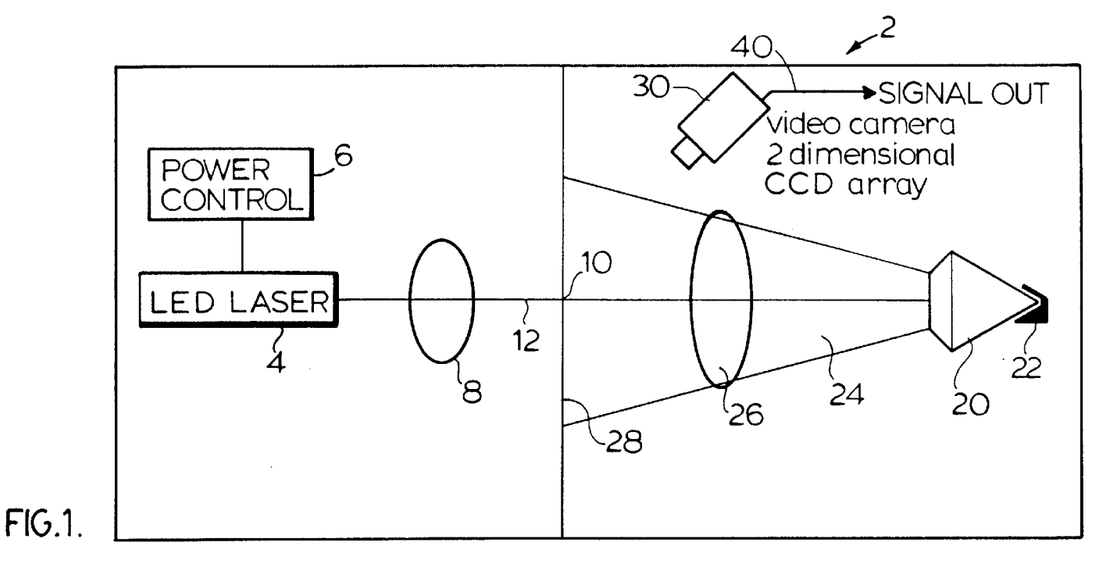
FIG. 1 is a schematic of the apparatus for producing an optical pattern by exposing a gemstone to a beam of light.

The gemstone scanner 2 has a solid state laser diode 4 which cooperates with a first optical arrangement 8 to produce a collimated focused laser light beam 12. The optical arrangement 8 adapts this type of laser to the required focused, precise light beam suitable for this application. This light beam passes through a narrow emitting port 10 in the screen 28. The collimated beam 12 passes through the optical arrangement 26 and strikes a gemstone 20 held in the gemstone fixture 22. The gemstone is orientated such that the table of the gemstone is perpendicular to the light beam 12.

The gemstone 20 reflects and refracts the collimated beam 12 and produces an optical output response, generally shown as 24, comprising reflected and refracted light in a unique pattern. This output passes through the second optical arrangement 26 and is focused on the screen 28.

Each gemstone, due to the inherent properties of the gemstone and the cutting of the gemstone, produces a unique optical response which can be distinguished from the optical response from other gemstones. As each gemstone is aligned in the fixture and centered relative to the beam, the optical response is inherent to the gemstone such that the optical pattern is consistent. This optical pattern, however, will be at a different rotational position relative to the axis of the light beam if the position within the fixture has changed.

A two-dimensional CCD (charge couple device) video camera 30 is positioned to one side of the scanner and is directed at the screen 28. The two-dimensional CCD camera is adjusted to cover the focused optical response 24 provided on the screen 28, allowing this entire image to be captured at the same point in time. The screen 28 includes four LEDs 61 located in fixed corner positions of the screen. These known precise positions are used to correct for the angular offset of the camera 30 and determine the center of the image.

Figure 2:
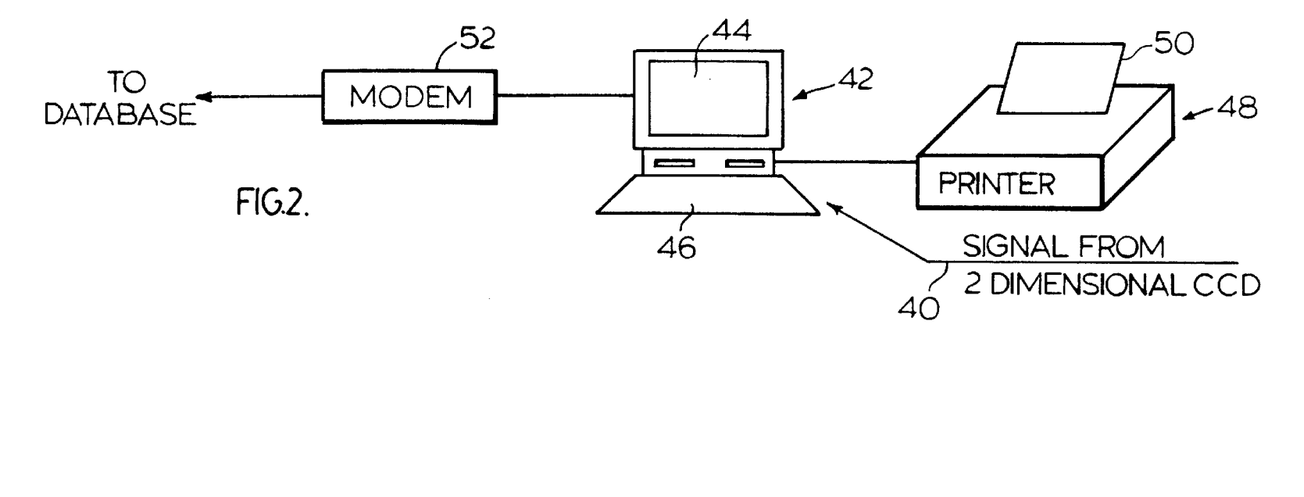
FIG. 2 is a schematic of various apparatus for processing the signal from the optical device.

The two-dimensional CCD camera 30 produces a video output signal 40 which is fed to the personal computer 42 shown in FIG. 2. The personal computer 42 includes a video frame grabber card and associated software memory storage, a display screen 44, a keyboard 46, image processing software and a counter. Associated with the personal computer is the printer 48 which prints gemstone certificates 50. In addition, the personal computer includes a modem 52 which communicates to a database over the public switched telephone network.

The counter is used to maintain a check on optical images recorded in the database and is indexed for each recordal. This count is also kept with the database whereby departures in the sequence can be identified and investigated.

Figure 4:
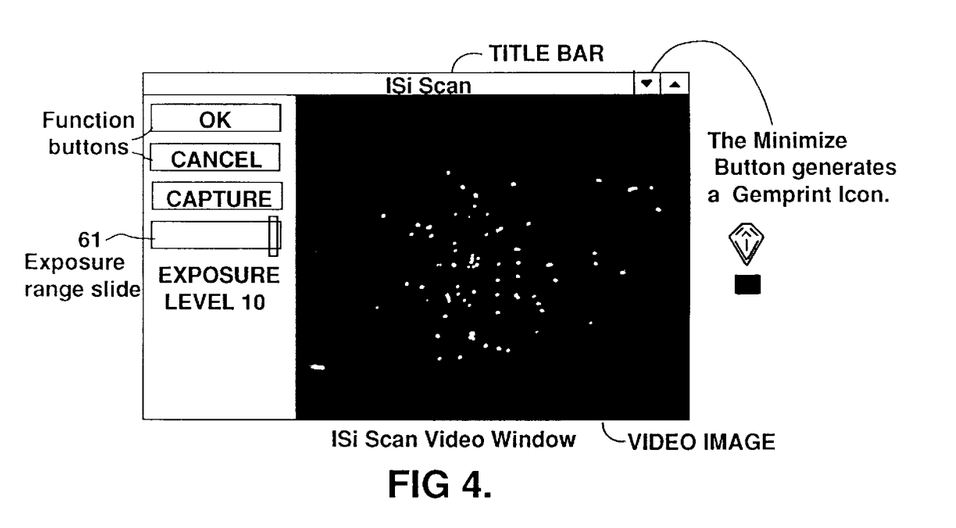
FIG. 4 shows an initial optical pattern from the camera and operator controls displayed on the screen.

The processing software of the personal computer 42 allows proper identification of the owner of the gemstone, followed by details of the gemstone as assessed by a jeweller. Details of the gemstone include the cut, clarity, colour and other characteristics. This information is keyed in using the keyboard 46. The video signal 40 from the two-dimensional CCD camera is displayed on the display screen 44 using a 256 gray scale (see FIG. 4). The scanner 2 is actually in an enclosure, as the display of the optical response from the gemstone is dependent upon ambient conditions, such as light conditions. The jeweller conducting the gemstone identification reviews the optical response on the display screen 44 and if he determines that the gemstone requires additional power for increased clarity, he adjusts an exposure control slide displayed on the computer screen. Adjustment of this control varies the power of the diode laser. This type of laser is easily adjustable to a host of power settings and allows the jeweller a further variable for controlling the quality of the final optical response. Too much light causes "blooming" in the video capture of the optical response and therefore less accuracy. Not enough power results in loss of low level responses from the gemstone. It is generally preferred to adjust towards a low level while maintaining the number of "hot points" in the optical response. The 256 gray scale allows detection of the boundary or edges of the various points and accurately locates and sizes them. One such video image is shown in FIG. 4 as it is displayed on the display screen together with the function buttons "OK", "CANCEL", "CAPTURE" and the "EXPOSURE LEVEL" slide control 61. The video image has "hot points" shown as white areas and the black area is the background screen 28.

The "CAPTURE" button is used to indicate the image is suitable and should be recorded and the associated process completed.

Figure 5:
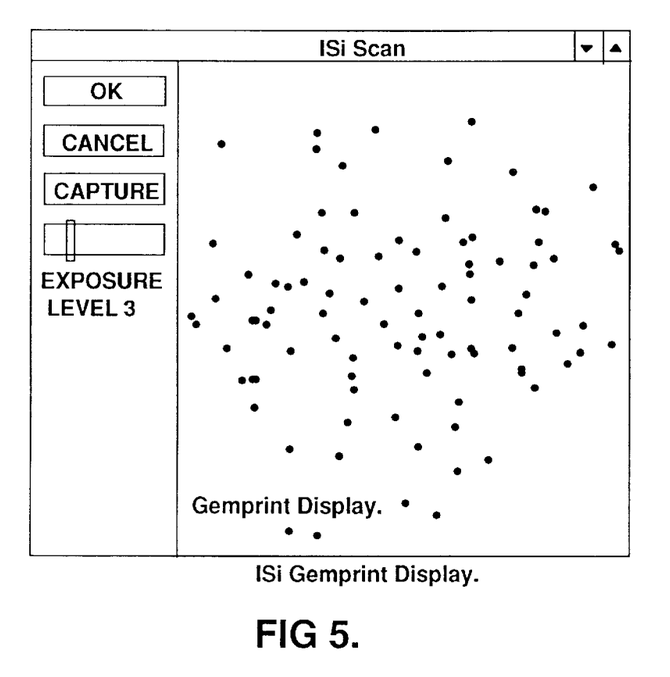
FIG. 5 is a display of a simplified corrected image for recordal based on the initial optical pattern.

The gemstone scanner 2 and the personal computer 42 allows a jeweller to examine the video image of a properly located gemstone and adjusts the power of the laser by using the exposure control slide 61 displayed on the computer screen. The jeweller thus adjusts the power of the laser to a level for optimum image capture. The video or initial image of FIG. 4 uses a 256 level gray scale and changes in exposure are immediately reflected in the displayed image. The 256 gray scale provides very good accuracy in distinguishing between areas which are reflected or refracted light beams and areas which do not have any significant light response. Once the jeweller has adjusted the device and is satisfied that the video image would be suitable for recording, he actuates the "CAPTURE" button. This CAPTURE step takes him to the next level of the program and procedure where various corrections to the image are implemented and the images have been simplified to a monochromatic display. This second level of image capture and display is shown in FIG. 5. In this case, the "hot spots" are now shown as black areas and the remaining area is white. As shown on the screen, there is a number of function buttons, namely "OK", "CANCELLED", and "CAPTURED", as well as an "EXPOSURE LEVEL" slide. This display has also undergone a number of corrections, one of which is for the angle at which the camera is located relative to the display screen. In addition, certain corrections for the LEDs and factors introduced by the particular scanner are also made. These corrections are determined upon start-up of the scanner. The LEDs produce hot spots in the image, but serve the useful purpose of locating the center of the image. During start-up, a background image is captured which includes the effect of these LEDs and other characteristics of the particular scanner and is stored. These effects can then be removed to leave a captured image more accurately reflecting the characteristics of the gemstone.

With the images shown in FIG. 5, the jeweller then has the option to confirm that the image is appropriate for recordal and if this is the case, he would execute the CAPTURE button. This image is then combined with the inputted information regarding the identity of the owner and the various characteristics of the gemstone for recordal purposes. It is also possible at that time to provide a certificate of this optical display, the identity of the owner and gemstone characteristics.

The display of FIG. 5 is greatly simplified relative to the video display of FIG. 4. FIG. 4 has 256 levels of distinction whereas FIG. 5 is basically either white or black. The computer 42 includes pattern matching software and edge detection software for taking the image of FIG. 4 and converting it and simplifying it to the image of FIG. 5. The purpose of this simplification is to reduce the amount of information stored and this reduced image is more than satisfactory for identification of the gemstone.

On occasion, what the jeweller considered to be an acceptable video image does not produce an acceptable simplified image of FIG. 5. In this case, the jeweller can adjust the exposure control and he is returned to the video display capture of FIG. 4. It is also possible to execute the CANCEL button and to stop the entire process, such that he can start again or merely abandon the process. Once the CAPTURE button has been executed, the OKAY button is activated causing interaction with a gemstone appraisal program, which will be subsequently discussed. Associated with the capture step is the eventual transmission of the information to a remote database.

The present system can be used by the jeweller in a number of different ways. The most simplified and common service provided by the jeweller is with respect to gemstone identification and recordal. In this case, the owner of the gemstone wishes to have the gemstone properly identified by its optical image as well as the physical characteristics of the stone and have this combined information recorded in a centralized database. In this way, the user knows that his stone has been accurately "fingerprinted" and this record is maintained in a central database for future retrieval. If the gemstone is stolen, the optical image may be transferred to a database of stolen gemstones and any recovered gemstones can be cross-checked against this database. One of the major problems is matching recovered stolen gemstones with their owner. This problem is overcome by the above arrangement where the stolen gemstone database is searchable by the police.

A further service provided by the jeweller allows verification of gemstones and can be used by the jeweller with respect to jewellry repair. A client wishing to have stone repaired or a setting fixed may be required to leave the gemstone with the jeweller. This can cause certain apprehension for the customer, as there have been occurrences of gemstones being fraudulently replaced with less valuable stones. To provide a level of confidence for both the customer and the jeweller, the jeweller use the system to perform a verification process. The verification process involves going through the various steps to provide an optical capture of the gemstone (simplified and corrected image) together with the particulars and owner of the stone. This information can be printed for both the jeweller and the customer. In contrast to the recordal system described above, this optical image is maintained in a verification database by the personal computer. The jeweller and customer can also sign these images as a form of acknowledgement.

Figures 6, 7:
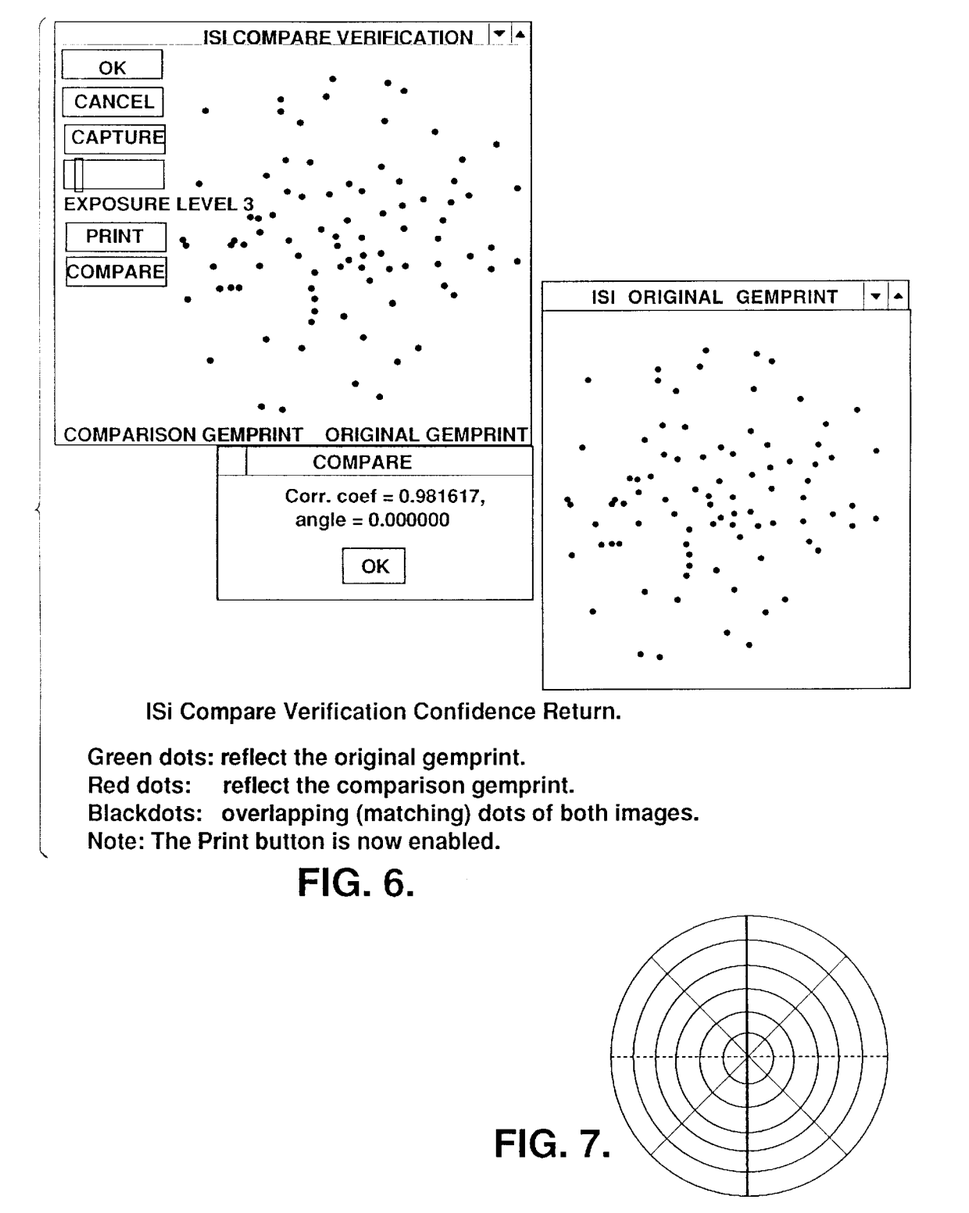
FIG. 6 shows the verification screen.
FIG. 7 shows a simplified approximation of the coding arrangement.

When a customer returns to pick up the repaired jewellry, a second optical image is captured and this optical image is displayed on the computer screen. The jeweller then recalls the earlier captured image and also has it displayed on the screen. Although the first and second optical images are the same, their will be an angle of rotation therebetween which must be identified to allow the optical images to be accurately compared. The personal computer has recorded each of these images in a way to allow identification of this angular rotation, allowing one image to be overlapped relative to the other. The computer display screen then displays the overlapped images or combined images with areas of "hot spot" agreement being identified by one colour, and points of disagreement being of a different colour. In addition, the software of the computer also provides a match coefficient, which is basically a correlation coefficient showing the degree of similarity between the two displays when properly rotated. Thus, the system provides both a visual indication as well as a calculated degree of match between the two images. An example of the display to establish verification is shown in FIG. 6. The image in the upper right is combined image and the image at the lower right is the original optical image. Note the correlation coefficient which provides an indication of the matched confidence.

With the above arrangement, both the jeweller and the customer are protected.

The scanner, upon start-up, goes through a calibration process as well as determination of correcting factors to be applied during the final image capture process. During start-up, the scanner, without a gemstone located therein, produces a number of images which are used to accurately locate the four LEDs and account for their optical response. The position of the LEDs are used to determine the necessary perspective correction for the camera. These four LEDs also precisely locate the center of the image. Any misalignment of the laser can result in a lightened area to one side of the center of the image and is present in these captured images. This lightened area is accounted for in the final image capture, as the effect has been determined and removed. It can also be appreciated that when the camera captures the image, the effect of the LEDs and any slight laser misalignment will be present in that image. This is basically corrected by determining an appropriate average "empty scan" and, in simplified terms, subtracting this from the captured image, thereby eliminating the effect of the LEDs and eliminating and minimizing any laser misalignment. It can be appreciated that this calibration process is an ongoing process, (i.e. it is carried out each time the scanner is activated) and thus reflects any minor changes that may have occurred to the scanner over time.

This calibration also determines scanner damage, which renders it unacceptable.

It can also be appreciated that the present invention allows the jeweller to optimize the initial video display of the optical response and allow adjustment thereto to improve the accuracy.

The present system can also be used to record appraisal of gemstones, which is now becoming more common and necessary if a gemstone is to be insured. In this case, the jeweller activates a further part of the computer software which is specifically directed to the gemstone appraisal program. Again, the jeweller goes through the necessary steps to capture the appropriate final optical image and key in the information with respect to the owner and the characteristics of the gemstone. The jeweller also enters his appraised value of the gemstone. This combined information is then downloaded via the modem to the national database and in particular, the appraisal data indicated as 9 in FIG. 3. The computer associated with the appraisal data 9 can compare the characteristics of the gemstone and the appraised value of the gemstone with industry standards or averages maintained by the database. The appraised value is normally accepted, however, if it departs significantly from industry standards or industry averages, the appraisal can be flagged. The most common case is that the appraised value may be somewhat high, as the jewelry market typically has a relatively high retail price from which there is a substantial discount. The insurance policies typically are for the insured value or replacement value, and therefore, a somewhat high appraisal is acceptable to the insurance company. This database of appraised values and characteristics of the gemstones can be used by the insurance company to reflect any increased value of the gemstones over time. For example, upon renewal of a policy, it may be appropriate to consider whether the appraised value should have risen, for example if that particular gemstone type has increased substantially in value. This computerized database can easily be used to provide this valuable information to the insurance company. Furthermore, the database provides an accurate record of the insured gemstone and if a gemstone is stolen or lost, the chances of retrieving the gemstone is improved, as it can be compared and identified with any recovered gemstones. The optical response allows identification and return of these gemstones to the proper owner or to the insurance company. As part of the assessment of the appraised value, the optical fingerprint does provide some indication of the quality of the stone. Therefore, this optical fingerprint can be used as a factor in confirming the appraised value.

Figure 3:
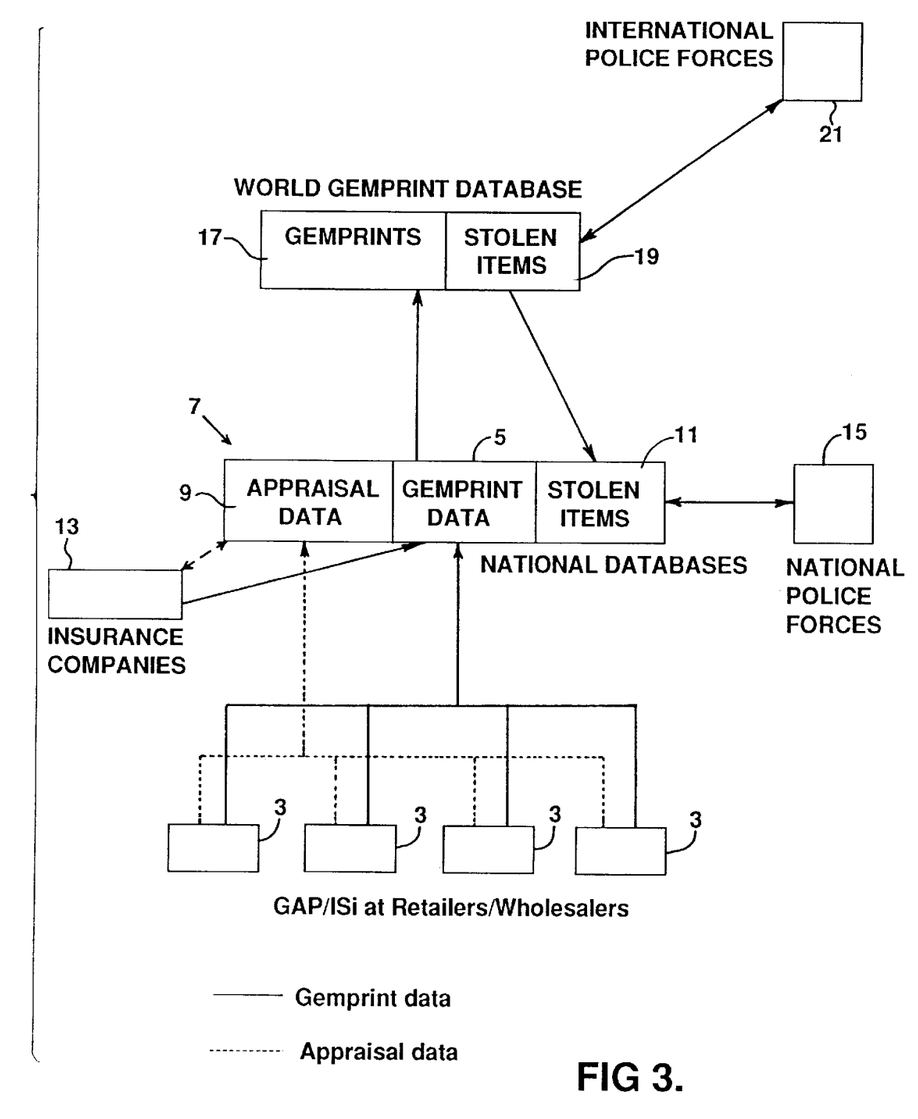
FIG. 3 is a schematic of the overall system.

FIG. 3 shows a further feature of the present invention where insurance companies and police forces can advantageously use information maintained in the database. A number of separate site scanners and personal computers are shown as 3, which interact with the public and carry out gemstone appraisal procedures and forwards the information to a gemstone database 5. In some cases, customers only wish to have the optical response characteristics of their gemstone maintained in a central database for subsequent reference. The recordal of these optical responses will assist in recovery of the gemstones should they be stolen and subsequently recovered by the police. It can be seen that the database, generally shown as 7, is divided into the gemstone optical data 5, the appraisal data 9 and the stolen data 11. The individual site arrangements 3 provide information to the gemstone data 5 as well as provide information to the appraisal data 9. For example, if the person purchasing the gemstone wishes to record the optical response and additionally record appraisal data with a particular insurance company, information is sent to both segments of the database 5 and 9. The insurance companies, generally indicated as 13, can access their portion of the appraisal data or the all of the appraisal data, depending upon the particular contractual relations therebetween. In addition, it can be seen that insurance companies can have various optical responses from gemstones recorded in the gemstone data 5.

When a gemstone has been recovered by the police and it is considered to be stolen, a police force, generally indicated as 15, can carry out their own scan of the gemstone using a scanner 2 and then search the database 11, which has the optical responses of all stolen gemstones. For example, when someone has a gemstone stolen and they have already had the optical response of the gemstone recorded in the database 5, they advise their insurance company. The database is advised and the optical response of the particular gemstone is copied to the stolen items database 11. Preferably, the databases 5, 9 and 11 are maintained on a national level, but they do interact with a further worldwide database which includes its own collective database of all optical responses, indicated as 17, as well as a stolen item portion identified as 19. This world portion of the database need not be constantly updated, but can be updated every day, every week, or every two-week period by receiving the new data from the national databases. This simplifies maintenance of the world database, although the national databases are somewhat more current. If a police force does not have success in identifying a stolen gemstone on a national database, they can refer to the international database and search the stolen items in the database 19. This can be done by national police forces and/or international police forces indicated as 21.

The computer database is contacted by the police and the appropriate optical responses of found gemstones download to the database. The database then determines whether there are any matches with the stolen gemstone database. A positive match or closest matches are then uploaded to the personal computer of the police scanner for verification, as described earlier.

From the above, it can be understood that the present system for recording of optical responses from gemstones and also maintenance of a database, which can be searched and also includes text description combined with optical responses for an accurate identification of the gemstone, is advantageous. Files are downloaded to the central database and the central database is also able to upload files to authorized systems, when appropriate. These files are text files combined with bit map images of the optical responses of the particular gemstones. With this arrangement, a police agency can download a file for a gemstone comparison to the central database and then receive a file containing the optional response and other information of a possible match in real time. It should be noted that with this arrangement, the user is then able to make his own assessment of whether there is an accurate match between the particular gemstone under consideration and the one located by the database. The database will provide its own match, but it does provide all of the information to the user's machine, allowing the optical responses to be placed side by side, whereby the user can make his own determination. As can be appreciated, some variation can occur due to the particular locating in the gemstone fixture and with this arrangement, the images can be manipulated and further visual evaluation can be made by the user.

The video camera to instantaneously captures the initial information in 256 gray scales and rapidly responds to changes in exposure setting. This captured image is then viewed on the computer monitor and allows the user to quickly evaluate the quality of the optical response and make appropriate adjustments (exposure adjustment), if necessary. The video camera also provides a more accurate method to capture the optical response, as the entire image is captured in two-dimensions around each photonic receptor in place of only one dimension, which was possible with older technology using line by line scanners.

The new scanner uses a laser diode which can easily be adjusted to vary the intensity of the light source and allows more control for adjusting to ambient conditions, such as ambient light conditions, and other factors such as the colour of the gemstone.

The combination of the laser diode and the two-dimensional CCD camera allows the user to have real time exposure control, whereby changes in exposure settings for different gemstones can be made. The scanner typically has a predetermined standard, but in certain circumstances, this needs to be varied to provide a more accurate optical response.

The personal computer is also provided with its digitization and comparison algorithm which allows comparison of gemstone optional response by the site system without downloading the file to the central database. In this way, gemstones and their optical responses can be separately compared and used as part of the verification process.

The new digitization and comparison algorithm uses a bin method to accurately and quickly compare two optional responses on the scanner. Histograms of the optical responses are created by measuring the number of black pixels that fall within specified bins. The bins are defined by dividing the captured optical response into a series of "pie slices" with each pie slice being further subdivided by a series of concentric rings placed about the center of the captured optical response (center can be determined due to the detected corner LEDs, the effect of which is removed). This is generally shown in FIG. 7.

Once the histograms of the two gemstones are determined, an angle of "best match" is determined by correlating the two histograms.

Next, one of the gemstones is rotated by the angle of best match. The two gemstone images are then "overlaid" by the computer, forming a single colour coded image. Red areas are hot spots resulting from one of the original gemstones; green areas are hot spots resulting from the other original gemstone, and black represents area of corresponding hot spots from the two original gemstones. The relative position of the two original gemstones forming the overlaid image can be "fine tuned" to maximize the amount of black appearing. This can be done manually via the computer keyboard, or automatically by the computer itself.

A gemstone match can be determined by evaluating the amount of black appearing on the overlaid image, with respect to the amount of red and green. More black represents a better match; less black indicates a poorer match. The evaluation can be performed visually or by computer, which produces and displays a match coefficient.

The present invention also allows a jeweller to produce jewelry appraisals and requires the collection of specific data. The appraisal information is then shipped with the optical response to the central database where the values are verified. Insurance companies now have a central database which can be accessed in the event of theft or loss. The accurate description collected by the appraisal at the site machine facilitates quick and accurate replacement of the gemstone. In addition, insurers can now automatically update the value of these appraisals and provide the insured with accurate insurance protection.

With reference to FIG. 1, the laser diode, the optical arrangements, the screen, the camera and the fixture are mounted on a fixed substrate and the alignment thereof are factory set.

The present invention has been described with respect to recording or producing optical images of gemstones. It can be appreciated that this technology is not limited to gemstones and can be used to produce an optical image of any matter which responds to the laser light beam stimulus in a similar manner. This arrangement could also be used for identifying gemstones produced in a particular manner which can be identified by the optical response of the gemstone. Therefore, the device can be used for other applications where the optical response is recorded and classified for other purposes than recordal.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A gemstone recordal system which records a unique light pattern of a gemstone comprising
    a site computer having means for receiving a data signal from a two-dimensional video camera,
    said two-dimensional video camera being part of a light image capture arrangement comprising
        a light emitting laser diode in combination with optical means for producing a collimated light beam directed at a gemstone fixture,
    said gemstone fixture orientating a gemstone in a predetermined manner relative to the collimated light beam, and a screen surface onto which the unique light pattern from a gemstone is collected,
    said video camera being directed at said screen surface and being sized to capture the unique pattern simultaneously,
    said computer correcting said signal from said video camera for known distortions introduced due to an angular position of said video camera relative to said screen surface and producing a digital signal of said unique pattern on said computer for review and approval by a user,
    said computer including means to have a user input and associate characteristics of the gemstone producing the image with said digital signal thereby producing a combined signal and a printer for producing a certificate identifying the characteristics and reproducing the corrected unique pattern,
    said computer forming a communication with a predetermined computer database and outputting said combined signal to said predetermined computer database which records said combined signal in a standardized manner.

2. A gemstone recordal system as claimed in claim 1 wherein said signal from said video camera is displayed on a display screen of said site computer.

3. A gemstone recordal system as claimed in claim 1 wherein a potential match using a host of radical sectors and a comparison of the number of points in corresponding radial sectors.

4. A gemstone recordal system as claimed in claim 1 wherein said predetermined computer database upon recordal of a combined signal transmits an acknowledgement signal back to the site computer.

5. A gemstone recordal system as claimed in claim 4 where the unique pattern is displayed in one colour and the original pattern is displayed in a contrasting colour.

6. A gemstone recordal system as claimed in claim 1 wherein said light emitting diode laser has an adjustable control for varying the output thereof to accommodate different light absorbing properties of gemstones and different ambient conditions.

7. A gemstone recordal system as claimed in claim 6 wherein said site computer evaluates each captured image and has an actuation control which adjusts said adjustable control means of said laser.

8. A gemstone recordal system as claimed in claim 1 including means for entering an appraised value of said gemstone at said site computer and said predetermined computer database reviewing said appraised value based on said characteristics and with reference to industry averages and accepts said appraised value when the appraised value is consistent with industry averages for a similar gemstone and otherwise flags the appraised value.

9. A gemstone recordal system as claimed in claim 8 wherein said predetermined computer database additionally analyses said predetermined pattern and uses said analysis as one factor for contributing to the decision to accept or query the appraisal.

10. A device for producing a reproducible identification pattern of a polished gemstone comprising
    light directing means for directing a collimated beam of light onto a gemstone orientated in a particular known manner to produce an optical output of the internal refraction and reflection characteristics of the gemstone, means for capturing a selected portion of the output in a manner to establish the relative size and location of the reflected light beams, wherein said capturing means is a video camera and said light directing means is a light emitting laser diode having associated therewith optical means for collimating the output.

11. A device as claimed in claim 10 wherein said light emitting laser diode has an adjustable power control for varying the light output thereof.

12. A method of recording an optical image of a suitable substance comprising:

producing and displaying an optical image of the substance which has been exposed to the output of a stimulating laser, initially capturing the optical output using a video camera, displaying the captured optical image and providing an exposure control which varies the output of the stimulating laser for improving definition of the optical image, approving a captured optical image for recordal, correcting the approved captured optical image for an angular orientation of the video camera relative to the displayed optical image, and simplifying and classifying the displayed optical image to precisely locate and size hot spots in the captured optical image and recorded the same in a digital signal, and store the digital signal in a database for future retrieval.

13. A method as claimed in claim 12 including providing a hard copy printout of the optical image corresponding to the digital signal.

* * * * *